United States Patent [19]

Takago et al.

[11] Patent Number: 5,288,889

[45] Date of Patent: Feb. 22, 1994

[54] FLUORINATED ORGANIC SILICON COMPOUNDS AND METHOD FOR MAKING

[75] Inventors: Toshio Takago; Shinichi Sato; Hitoshi Kinami, all of Annaka; Noriyuki Koike, Gunma, all of Japan

[73] Assignee: Shin-Etsu Chemical Co., Tokyo, Japan

[21] Appl. No.: 60,537

[22] Filed: May 13, 1993

[30] Foreign Application Priority Data

May 18, 1992 [JP] Japan .................... 4-149991

[51] Int. Cl.$^5$ .................... C07F 7/10
[52] U.S. Cl. .................... 556/419
[58] Field of Search .................... 556/419

[56] References Cited

U.S. PATENT DOCUMENTS

| | | |
|---|---|---|
| 3,646,085 | 2/1972 | Bartlett .................... 556/419 |
| 3,950,588 | 4/1976 | McDougal .................... 556/419 X |
| 4,094,911 | 6/1978 | Mitsch et al. .................... 556/419 X |
| 4,647,413 | 3/1987 | Savu .................... 556/419 X |
| 4,742,177 | 5/1988 | Yamamoto et al. .................... 556/419 |
| 4,927,950 | 5/1990 | Hisamoto et al. .................... 556/419 |
| 5,124,467 | 6/1992 | Rodgers et al. .................... 556/419 X |
| 5,166,383 | 11/1992 | Parrinello et al. .................... 556/419 X |

*Primary Examiner*—Paul F. Shaver
*Attorney, Agent, or Firm*—Birch, Stewart Kolasch & Birch

[57] ABSTRACT

A fluorinated organic silicon compound of a structure having a fluorinated polyether group in its backbone and an isopropenoxysilyl group attached at either end forms a compliant coating on the surface of any substrate such as silicone rubber which is effective in imparting water and oil repellency and stain resistance to silicone rubber surface.

2 Claims, 1 Drawing Sheet

FLUORINATED ORGANIC SILICON COMPOUNDS AND METHOD FOR MAKING

BACKGROUND OF THE INVENTION

1. Field of the Invention

This invention relates to novel fluorinated organic silicon compounds having water and oil repellency and stain resistance and a method for preparing the same.

1. Prior Art

Several fluorinated organic silicon compounds are known as surface treating agents having water and oil repellency and stain resistance. Their typical examples are the following compounds.

$$CF_3(CF_2)_7CH_2CH_2Si(OCH_3)_3$$

$$CF_3CF_2CF_2OCFCF_2OCFCONHCH_2CH_2CH_2Si(OCH_3)_3$$
$$\quad\quad\quad\quad\;\;|\quad\quad\;\;|$$
$$\quad\quad\quad\quad CF_3\quad CF_3$$

$$CF_3(CF_2)_7CH_2CH_2Si(NH)_{\tfrac{3}{2}}$$

These compounds are successful in providing water and oil repellency and stain resistance to hard stationary surfaces such as glass and plastics. These compounds, however, are not fully effective agents for treating the surface of elastic members such as silicone rubber since they form less flexible coatings.

SUMMARY OF THE INVENTION

Therefore, an object of the present invention is to provide a novel fluorinated organic silicon compound which is applicable to elastic members such as silicone rubbers for surface treatment for imparting water and oil repellency and stain resistance as well as a method for preparing the same.

The inventors have found that a novel fluorinated organic silicon compound having a fluorinated polyether group and an isopropenoxysilyl group represented by the general formula (1) is obtained by reacting a perfluoropolyether compound of formula (2) with methanol to form a compound of formula (3), reacting it with allylamine to form a compound of formula (4), and reacting it with diisopropenoxymethylsilane or triisopropenoxysilane in the presence of a platinum catalyst such as chloroplatinic acid in accordance with the following reaction scheme.

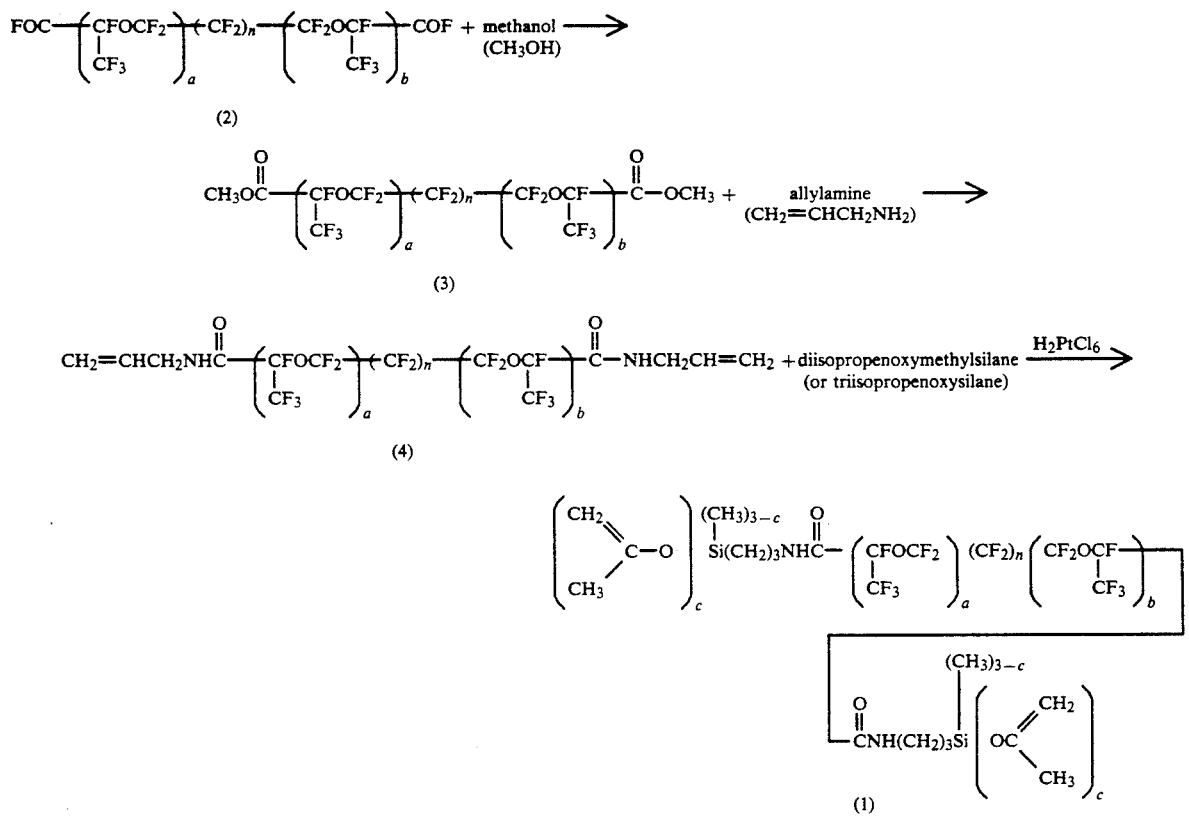

In the formulae, a and b each are an integer of 0 to 30, n is an integer of 0 to 10, when both or either one of a and b is 0, and c is equal to 2 or 3.

The fluorinated organic silicon compound of formula (1) is applicable to silicone rubber to form a compliant coating for imparting water and oil repellency and stain resistance to silicone rubber surfaces, which is unattainable with conventional surface treating agents. Also the compound may be added to silicone rubber for rendering its surface stain resistant.

DETAILED DESCRIPTION OF THE INVENTION

Figure 1:
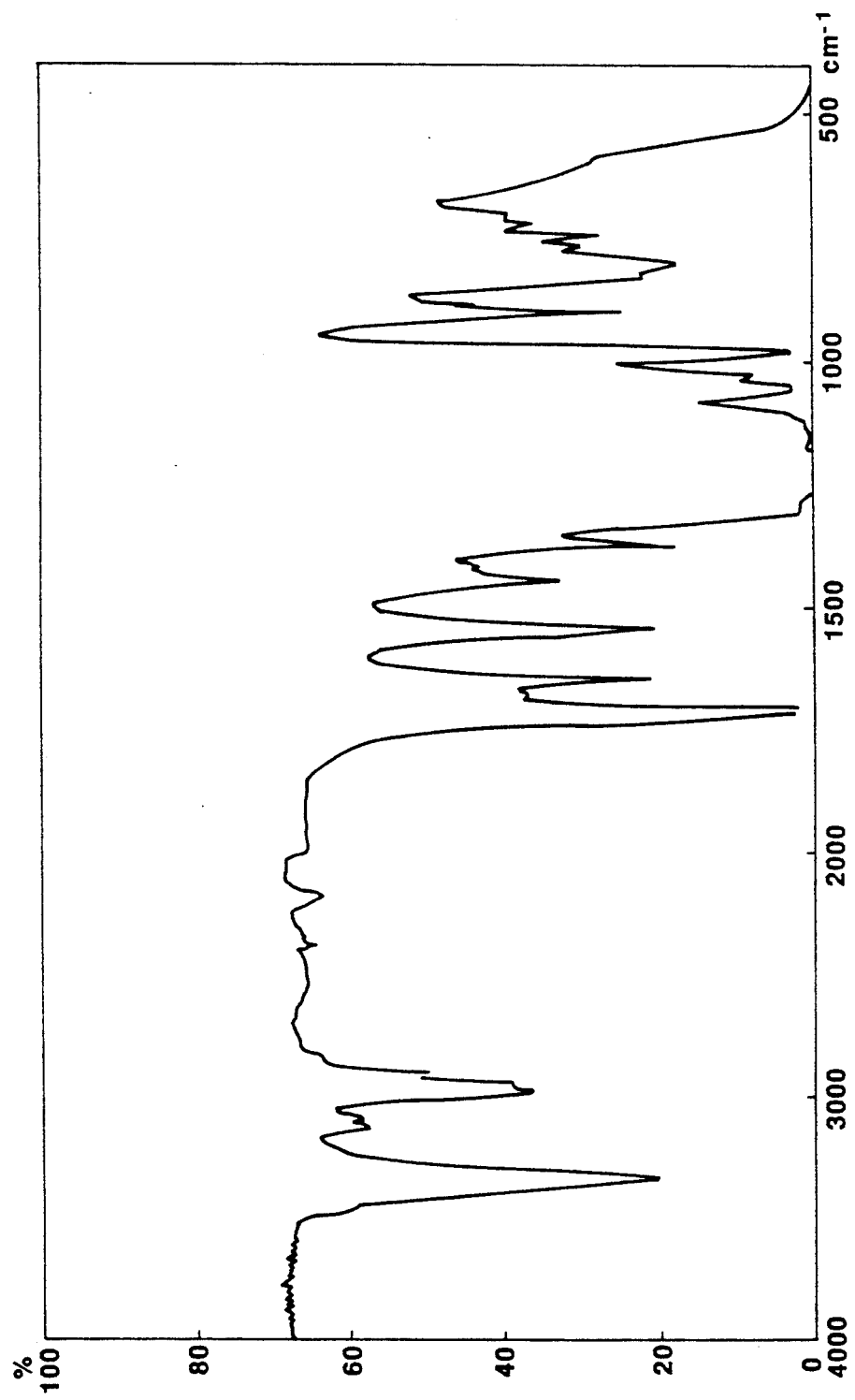
FIG. 1 is an infrared absorption spectrum of the fluorinated organic silicon compound obtained in Example.

The fluorinated organic silicon compound of the present invention is of a structure having a fluorinated polyether group in its backbone and an isopropenoxysilyl group attached at either end as represented by the following general formula (1).

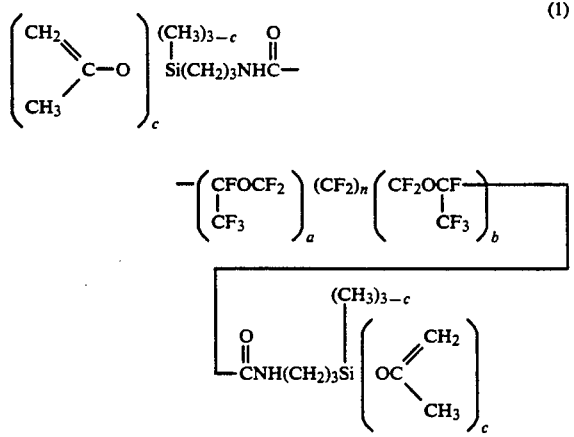

In the formula, each of letters a and b is an integer of 0 to 30, preferably an integer of 1 to 15 because compounds with too large values of a and b are difficult to prepare and have less affinity to substrate surfaces. Letter n is an integer of 0 to 10, often an integer of 0 to 4, and n is at least 1 when both or either one of a and b is 0. Letter c is equal to 2 or 3.

The compound of formula (1) can be synthesized by reacting a compound of the following general formula (4) with diisopropenoxymethylsilane or triisopropenoxysilane in the presence of a platinum catalyst such as chloroplatinic acid ($H_2PtCl_6$)

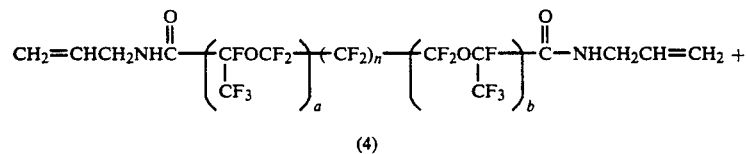

For this reaction, $1 \times 10^{-5}$ mol of the platinum catalyst and 2.2 to 3 mol of diisopropenoxymethylsilane or triisopropenoxysilane are preferably used per mol of the compound of formula (4). Reaction is effected at a temperature of 30° to 90° C. for about 2 to 30 hours. Fluorinated organic solvents are often used as the solvent with 1,3-bistrifluoromethylbenzene and 1,4-bistrifluoromethylbenzene being preferred.

The compound of formula (4) is, in turn, obtained by reacting perfluorodicarboxylic fluoride with hexafluoropropylene oxide in the presence of an alkali metal fluoride and an aprotic polar solvent to form a perfluoropolyether compound of formula (2) (see J. Macromol. Sci. Chem., A8, 3, pp. 499, 1974), reacting the compound of formula (2) with methanol to form a compound of formula (3) and reacting the compound of formula (3) with allylamine to form a compound of formula (4).

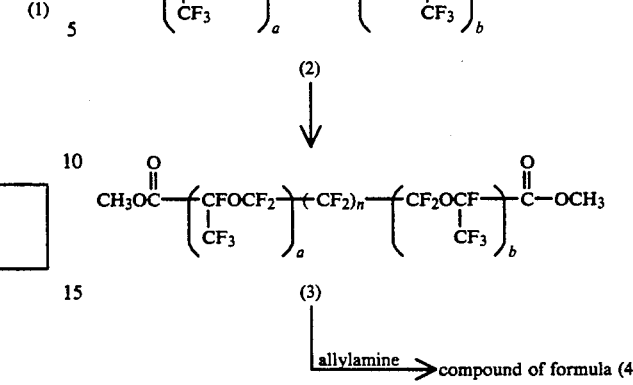

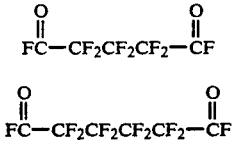

Examples of the perfluorodicarboxylic fluoride from which the perfluoropolyether compound of formula (2) is produced include compounds of the following formulae.

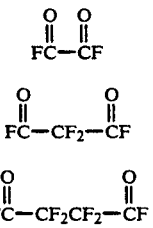

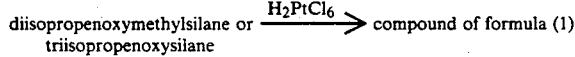

The reaction of the perfluoropolyether compound of formula (2) with methanol uses 3 to 30 mol of methanol per mol of the compound of formula (2) and takes place at a temperature of 20° to 30° C. for 1 to 5 hours.

The last reaction of the compound of formula (3) with allylamine uses 2.2 to 3 mol of allylamine per mol of the compound of formula (3) and takes place at a temperature of 20° to 60° C. for 1 to 5 hours. There may be used solvents such as 1,3-bistrifluoromethylbenzene and 1,4-bistrifluoromethylbenzene.

The fluorinated organic silicon compound of the invention is applied to a substrate or support and allowed to stand in the atmosphere to form a coating which is water and oil repellent, stain resistant, and flexible or compliant to the substrate. The inventive compound is an effective surface treating agent which can provide water and oil repellency and stain resistance to silicone rubber surfaces which could not be effectively altered with conventional surface treating agents. Alternatively, the inventive compound is added to silicone rubber whereby the silicone rubber is modified to be resistant against stain on its surface.

There has been described a fluorinated organic silicon compound of a structure having a fluorinated polyether group in its backbone and an isopropenoxysilyl group attached at either end which can form a compliant coating on the surface of any substrate such as silicone rubber. A coating of the compound is effective in imparting water and oil repellency and stain resistance to silicone rubber surfaces. The method of the invention ensures preparation of such fluorinated organic silicon compounds in high yields.

EXAMPLE

Examples of the present invention are given below by way of illustration and not by way of limitation.

Example 1

To a flask charged with 300 grams of a perfluoropolyether compound of formula (2') shown below and 40 grams of sodium fluoride, 200 grams of methanol was added dropwise.

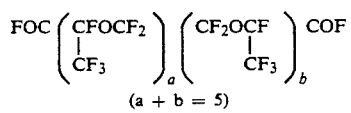

(2')

(a + b = 5)

At the end of addition, the reaction mixture was cooled and removed of the sodium fluoride by filtration and the filtrate was washed with water. During distillation of the filtrate, a fraction having a boiling point of 111.7° C. under a vacuum of 2 mmHg was collected, obtaining 250 grams of a product of the following formula (3').

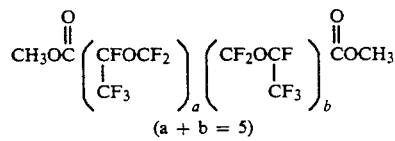

(3')

(a + b = 5)

A flask was charged with 120 grams of the product of formula (3') and 18.0 grams of allylamine. The contents were agitated for 3 hours while the reaction temperature increased to 45° C. at maximum due to exothermic reaction. At the end of reaction, the excess allylamine was removed by distillation, obtaining 115 grams of a non-volatile matter which was a compound having the structure of formula (4').

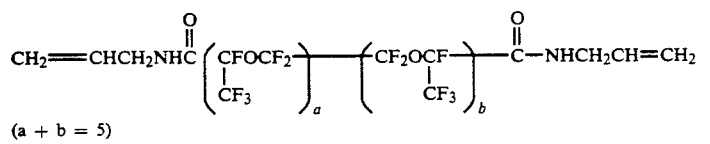

(4')

(a + b = 5)

A flask was charged with 30 grams of the compound of formula (4'), 20 grams of 1,3-bistrifluoromethylbenzene and 12 mg of $H_2PtCl_6$ and heated to 70° C. With stirring, 11.5 grams of diisopropenoxysilane was added. The temperature was raised to 80° C. and agitation was continued for 5 hours. After the completion of the reaction, 1 gram of active carbon was added to the reaction mixture, which was agitated for 3 hours. The active carbon was removed by filtration and the filtrate was stripped, obtaining 36 grams of a non-volatile matter as a fraction at 120° C. under a vacuum of 2 mmHg. By proton NMR, IR and elemental analysis, this compound was identified to have the following structure. FIG. 1 is the IR spectrum of this compound.

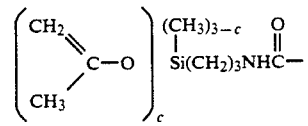

(a + b = 5)

| $^1$H-NMR | | |
|---|---|---|
| δ (ppm) | Si—CH$_3$ | 0.23 |
| | Si—CH$_2$ | 0.73 |
| | C—CH$_2$—C | 1.63 |
| | CH$_3$—C | 1.76 |
| | N—CH$_2$ | 3.31 |
| | C=CH$_2$ | 4.21 |

| IR |
|---|
| 3450 cm$^{-1}$ (H—N) |
| 1710, 1540 cm$^{-1}$ (\C=O) |
| 1645 cm$^{-1}$ (C=C) |

| Elemental analysis | | | | | | |
|---|---|---|---|---|---|---|
| | C | H | N | O | F | Si |
| Calcd. (%) | 34.3 | 1.5 | 2.2 | 13.6 | 44.1 | 4.3 |
| Found (%) | 34.5 | 1.7 | 2.0 | 13.4 | 44.7 | 3.7 |

Although some preferred embodiments have been described, many modifications and variations may be made thereto in the light of the above teachings. It is therefore to be undrestood that within the scope of the appended claims, the invention may be practiced otherwise than as specifically described.

What is claimed is:

1. A fluorinated organic silicon compound of the following general formula (1):

(1)

-continued

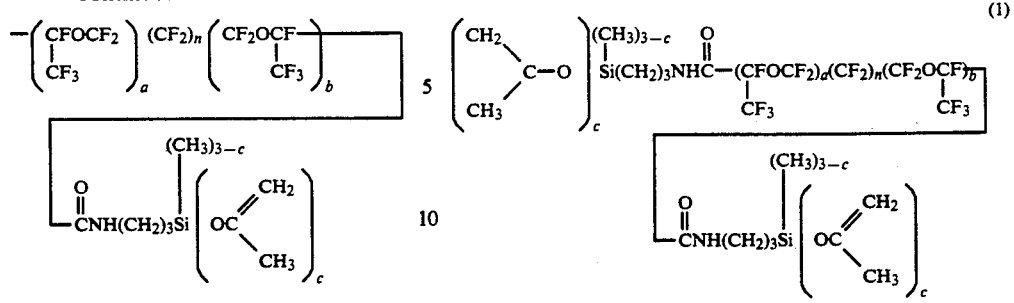

wherein a and b each are an integer of 0 to 30, n is an integer of 0 to 10, with the proviso that n is an integer of 1 to 10 when both or either one of a and b is 0, and c is equal to 2 or 3.

2. A method for preparing a fluorinated organic silicon compound of the following general formula (1):

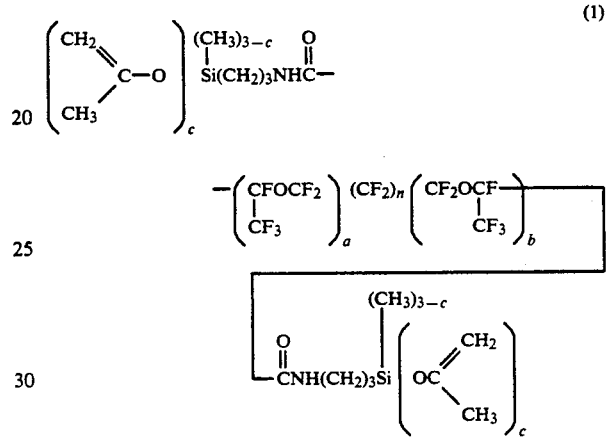

wherein a and b each are an integer of 0 to 30, n is an integer of 0 to 10, with proviso that n is an integer of 1 to 10 when both or either one of a and b is 0, and c is equal to 2 or 3, said method comprising the step of reacting a compound of the following general formula (4):

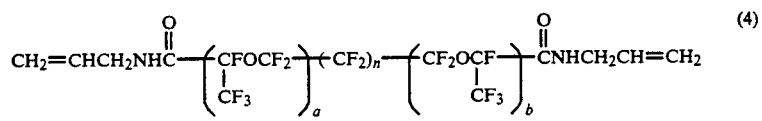

wherein a, b and n are as defined above with diisopropenoxymethylsilane or triisopropenoxysilane.

* * * * *